US00PP11547P

United States Patent [19]

Boeder

[11] Patent Number: Plant 11,547

[45] Date of Patent: Oct. 3, 2000

[54] CHRYSANTHEMUM PLANT NAMED 'RED ABOUT TIME'

[75] Inventor: Mark Boeder, West Wittering, United Kingdom

[73] Assignee: Cleangro Limited, West Sussex, United Kingdom

[21] Appl. No.: 09/133,900

[22] Filed: Aug. 13, 1998

[51] Int. Cl.[7] ..... A01H 5/00

[52] U.S. Cl. ..... Plt./293

[58] Field of Search ..... Plt./293, 287

*Primary Examiner*—Howard J. Locker

*Attorney, Agent, or Firm*—Christie, Parker & Hale, LLP

[57] ABSTRACT

A new variety of chrysanthemum producing red flowers.

1 Drawing Sheet

BACKGROUND OF THE INVENTION

The Present invention is directed to a new and distinct variety of chrysanthemum botonically classified as *Dendranthema grandiflora*. The varietal denomination of the new chrysanthemum is 'Red About Time'.

The new variety was discovered as a natural single branch sport in a cultivated planting of the variety 'About Time' (unpatented). The new variety has been asexually reproduced by vegetative cuttings in Ventura County, Calif. and the distinguishing characteristics are retained through successive generations of asexual reproduction.

SUMMARY OF THE INVENTION

'Red About Time' is pot type chrysanthemum plant variety that produces red flowers with flat capitulum form and abundant dark green foliage.

COMPARISON WITH PARENT

Flowers of the new variety are red and flowers of the parent 'About Time' are coral pink.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'Red About Time' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Red About Time' is about 20 days with the response time of about 8.5 weeks. One treatment with growth regulator B9 at 2500 ppm is useful. Desirable growing conditions include average night temperatures of about 18° to 20° C., and day temperature of about 20° to 30°C. The plants described were given one application of growth regulator B-9 at a rate of 1500 ppm.

Plant:

*Habit.*—Upright, herbaceous perennial.

*Height.*—26 cm.

*Number of breaks from pinch.*—4 to 5.

*Typical container sizes commercially grown in.*—16 cm pots.

*Length of lateral branches.*—21 cm.

*Stem color.*—138A.

Foliage:

*Leaf arrangement.*—Alternate.

*Number of leaves per lateral branch.*—11 fully expanded leaves.

*Leaf size.*—Length: About 7 cm. Width: About 4.8 cm.

*Leaf shape.*—Ovate.

*Attachment.*—Petioled.

*Leaf apex.*—Acute.

*Base.*—Tapered, truncate.

*Margin.*—Palmately lobed.

*Aspect.*—Flat.

*Surfae.*—Top: Lightly pubescent. Bottom: Pubescent.

*Midvein color.*—Underside: Near 137C. Upperside: Near 146C.

*Petiole.*—Length: About 1.5 cm. Color: Near 145A.

*Color.*—Mature leaf: Top: Near 147A. Bottom: Near 137B. Young leaf: Top: Near 137A. Bottom: Near 137C.

Bloom:

*Inflorescence form.*—Cyme.

*Flower type.*—Decorative.

*Number of blooms per branch.*—About 7.

*Diameter of fully expanded bloom.*—About 7 cm.

*Depth of fully expanded bloom.*—About 2.2 cm.

*Sepal number.*—About 75. Color: Near 137C. Length: About 1 cm. Width: About 0.5 cm.

*Peduncle.*—Length: Uppermost peduncle: About 3 cm. Lateral peduncle: About 8.5 cm. Habit: Straight. Surface: Pubescent. Color: Near 137C.

*Flower bud* (*when just showing color*).—Color: Near 181C. Diameter: About 1 cm. Height: About 1 cm. Shape: Spherical.

*Ray florets.*—Number per flower: About 170. Texture: Matte. Shape: Oblanceolate. Apex: 3 to 4 obtuse irregular lobes. Base: Tapered. Margin: Entire. Aspect: Slightly incurved, undulating. Length: About 3.4 cm. Width: About 1.1 cm.

*Disc florets.*—Number per flower: About 5. Texture: Shiny. Shape: Cylindric. Length: About 0.4 cm. Width: About 0.8 cm.

*Fragrance.*—Faint.

Flower color:

*General flower coloration.*—Red decorative.

*Ray florets, top side.*—Immature: Near 47A. Mature: Near 43A. Fading: Near 44C.

*Ray floret, under side.*—Immature: Near 47A. Mature: Near 44C. Fading: Near 42C.

*Disc florets.*—Immature: Near 145B. Mature: Near 2B. Fading: Near 16B.

*Changes as the flower ages.*—Flower color fades slightly, flower form remains flat.

Reproductive organs:

*Ray florets.*—Pistillate. Stigma shape: 2 branched. Stigma color: Near 2B. Style length: About 0.5 cm. Style color: Near 154C.

*Disc florets.*—Stigma shape: Linear. Stigma color: Near 1A. Style length: About 0.3 cm. Style color: Near 1D. Stamen number: About 5. Anther length: About 0.2 cm. Pollen color: Near 13B. Pollen quantity: Moderate.

What is claimed is:

1. A new and distinct chrysanthemum plant of the variety substantially as herein shown and described.

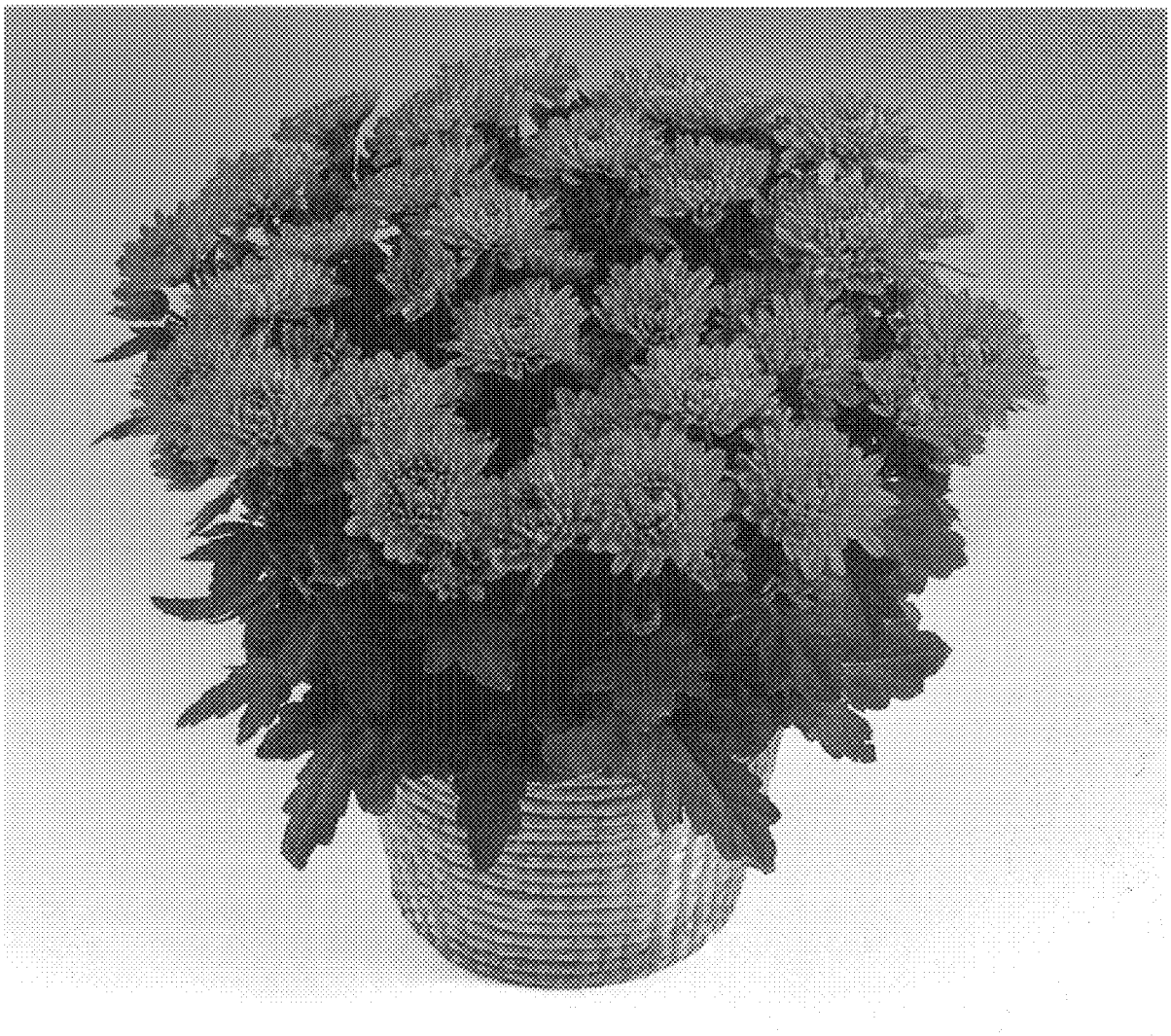

* * * * *